United States Patent [19]

Muller et al.

[11] Patent Number: 4,719,239
[45] Date of Patent: Jan. 12, 1988

[54] PHARMACEUTICAL MULTICOMPONENT SYSTEMS AND METHOD OF PREPARING SAME

[76] Inventors: Bernd W. W. Muller, Schlotfeldtsberg 14a, 2302 Flintbek; Hans-Jurgen Franzky, von-Coels-Str. 1, 5100 Aachen; Claus-Jurgen Kölln, Eichofstr. 9, 2300 Kiel, all of Fed. Rep. of Germany

[21] Appl. No.: 704,424

[22] Filed: Feb. 22, 1985

[30] Foreign Application Priority Data

Feb. 23, 1984 [DE] Fed. Rep. of Germany ....... 3406497

[51] Int. Cl.$^4$ .............................................. A61K 47/00
[52] U.S. Cl. ...................................... 514/785; 514/938; 514/941; 514/942; 514/943; 514/962; 514/966; 514/967
[58] Field of Search ............... 514/785, 938, 941, 942, 514/943, 962, 967, 966

[56] References Cited

U.S. PATENT DOCUMENTS

| | | | |
|---|---|---|---|
| 4,073,943 | 2/1978 | Wretlind et al. | 514/772 |
| 4,146,499 | 3/1979 | Rosano | 252/186 |
| 4,184,978 | 1/1980 | France et al. | 514/785 |
| 4,422,952 | 12/1983 | Koulbonis et al. | 514/785 |
| 4,567,161 | 1/1986 | Posanski et al. | 514/23 |

FOREIGN PATENT DOCUMENTS

| | | |
|---|---|---|
| 0100443 | 2/1984 | European Pat. Off. |
| 2304392 | 10/1976 | France |
| 2502951 | 10/1982 | France |
| 1537530 | 12/1978 | United Kingdom |
| 2098865 | 12/1982 | United Kingdom |
| 2148711 | 4/1984 | United Kingdom |

OTHER PUBLICATIONS

Chem. Abstract 98: 40582w 1983.
Rimlinger, G., Chemical Abstracts, vol. 92, (1980), p. 333, No. 186335r.

*Primary Examiner*—J. R. Brown
*Assistant Examiner*—John W. Rollins, Jr.
*Attorney, Agent, or Firm*—Cushman, Darby & Cushman

[57] ABSTRACT

The invention relates to liquid, transparent, multicomponent systems for use in pharmaceutical products for cutaneous, peroral, vaginal and parenteral administration of pharmaceutical active agents. The multicomponent systems according to the invention contain the active agents in a solution of an oily and optionally an aqueous component in the presence of certain physiologically acceptable surfactants and cosurfactants. Under certain conditions, the cosurfactants can serve as oil components or the latter can optionally take over the cosurfactant function. The biological availability of the active agents applied in the form of the multicomponent systems according to the invention is much better than that of active agents applied in the form of known multicomponent systems.

25 Claims, 3 Drawing Figures

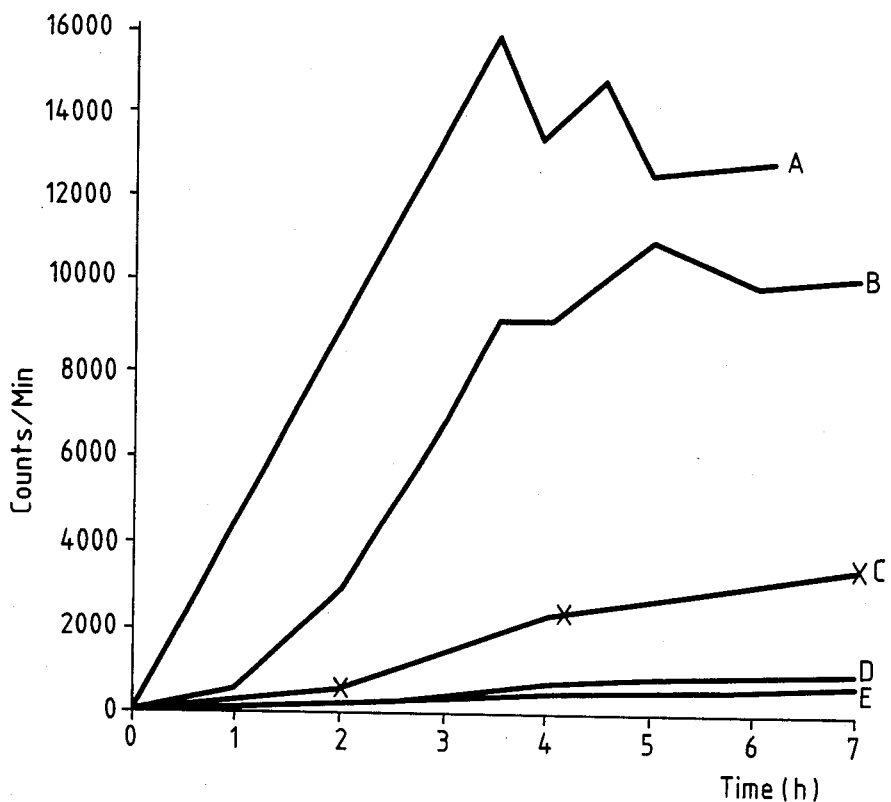
FIG.1 Serum level curves of tritium marked Arecaidin-n-propylester-HCl in the blood serum of rabbits following the subcutaneous application of identical active agent quantities in formulations A to E (see comparison example 1)

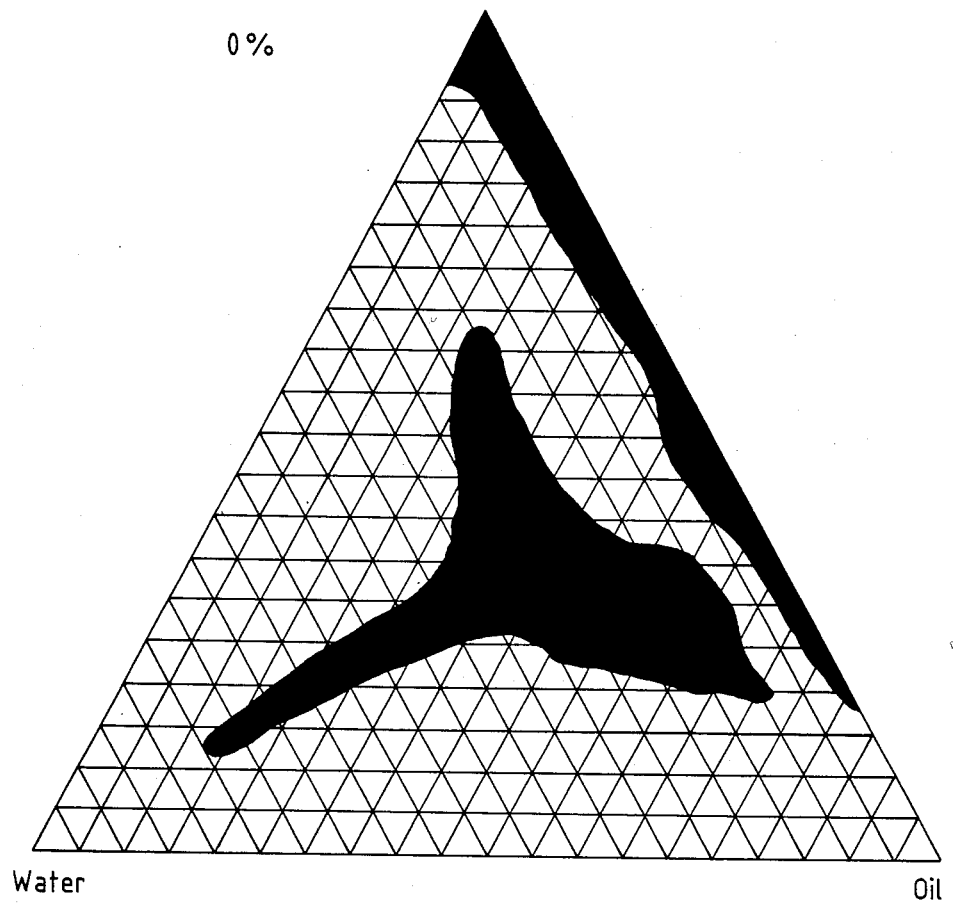
FIG. 2 Three-component diagram, the concentration areas in black are single-phase areas
PEG-glycerol monooleate 3 parts
Caprylic-capric acid glycerol esters 7 parts

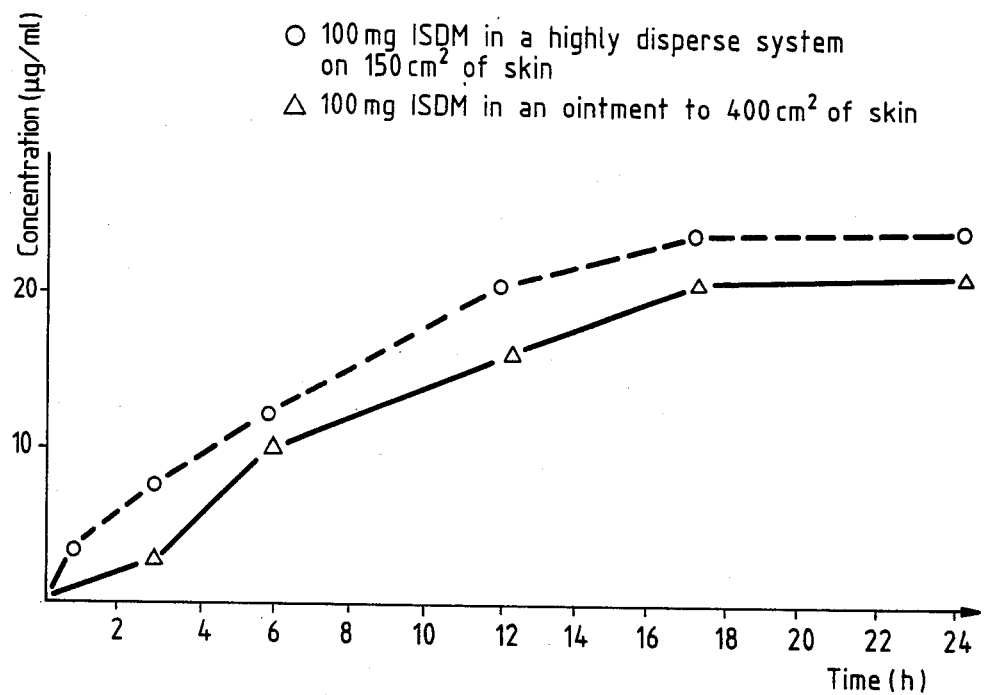

PHARMACEUTICAL MULTICOMPONENT SYSTEMS AND METHOD OF PREPARING SAME

The invention relates to liquid, transparent, pharmaceutically usable multicomponent systems.

The therapeutic activity of drugs is decisively influenced by the passive availability, namely the release from the applied system, as well as by the biological availability, namely the membrane passage of the active agent. The stage which takes place more slowly in each case determines the speed of absorption of the active agent by the organism. For example, in the case of cutaneous application, the active agent must be firstly released from the ointment and then penetrate the epidermis of the skin, before it is absorbed by a membrane and can be transferred. Generally, the passage through the epidermis is the slowest and consequently the speed-determining stage. It can be sped up by the choice of the ointment base, i.e. a water-in-oil (W/O) or an oil-in-water emulsion (O/W), or by incorporating penetrants. However, this possibility is restricted in that in the case of molecules with a molecular weight above 800, it is substantially impossible to exceed a penetration speed of $10^{-4} \mu g/cm^2 \cdot h$. As a result of its charge, the basal membrane of the corium also has a fixing or repelling action on all charged particles, so that e.g. dissociated substances cannot or can only penetrate to a very limited extent said cell layer. The membrane behaves in a similar way in the rectum. The dissolved active agent released by the administered drug must initially pass through the glycocalyx, before it can be absorbed by the cell membrane. If e.g. a diffusion into the cell layer is not possible as a result of an excessive molecular weight of the active agent, no significant absorption can take place. A limited absorption can also be achieved here through the addition of penetrants, but this is problemmatical for toxicological reasons.

Highly disperse, liquid, transparent, single-phase systems have long been known from chemical technology and have recently been described as a possibility for recovering residual oil from rough layers of the earth, cf D. O. Shah, "Surface Phenomena in Enhanced Oil Recovery", Plenum Press, New York, 1981. However, the pharmaceutical use of such systems has hitherto failed as a result of the toxicity of the ionic surfactants used. When using nonionic surfactants, such as polyethyleneglycol-(PEG)-sorbitol fatty acid esters, combined with fatty acids or fatty acid esters, only macroemulsions form at room temperature. Only at higher temperatures are microemulsions obtained in the phase inversion range, cf Shinoda, J. Colloid Interf. Sci. 32, 647, 1970. The use of this phenomenon was described for the first time by Ziegenmeyer and Führer, Acta Pharm. Techn. 26, 273, 1980. The authors brought tetracycline hydrochloride through the skin by setting the phase inversion temperature of the macroemulsion system, i.e. the reversal of the emulsion from a O/W to a W/O emulsion to the skin temperature of 32° C. However, such systems are not pharmaceutically usable as a result of their physical instability. In addition, the improvement of the skin penetration could only be demonstrated in an in vitro test with a therapeutically excessively low active agent concentration.

Microemulsion systems for use in foods were described by S. Friberg in "Food Emulsions", M. Dekker, New York, 1976. He contended that they were not emulsions, i.e. not conventional two-phase systems with a disperse phase, stabilized as a result of the interfacial potential and that they were in fact micellar solutions, i.e. mono-phase systems. However, the highly dispersed systems used by him were prepared with the aid of toxic surfactants.

The opinion that the systems are micellar, single-phase solutions is being increasingly expressed in more recent literature, cf J. D. Robb, "Microemulsions", Plenum Press, New York, 1982. However, the standard microemulsion systems with ionic or nonionic surfactants and cosurfactants of aliphatic, monohydric alcohols are always incorporated.

An aqueous microemulsion with skin-compatible adjuvants for pharmaceutical use is described in DE-OS No. 3,212,053. This specification claims emulsifier systems of esters of aliphatic ($C_3$–$C_{18}$) alcohols with aliphatic ($C_{10}$–$C_{22}$) carboxylic acids or aliphatic ($C_{12}$–$C_{22}$) alcohols as solvents, esters with at least one free hydroxyl group of a polyethylene glycol-(PEG)-glyceryl ether with 2 to 7 PEG units and an aliphatic ($C_6$–$C_{22}$) carboxylic acid or a monoether of a polyethylene glycol and an aliphatic ($C_{12}$–$C_{18}$) alcohol as emulsifiers, as well as aliphatic ($C_{12}$–$C_{22}$) alcohols or glycerol esters of aliphatic ($C_6$–$C_{22}$) carboxylic acids as coemulsifiers.

The description and examples of DE-OS 3,212,053 describe as the preferred embodiment aqueous microgels containing as the surfactant a monoether of PEG and an aliphatic ($C_{12}$–$C_{18}$) alcohol and as the cosurfactant an aliphatic ($C_{12}$–$C_{22}$) alcohol.

The combination of PEG ether and ester with aliphatic alcohols for reducing the surface tension to values below $1 \text{ mN m}^{-1}$ and consequently for the formation of so-called microemulsions is already described per se in the literature, cf B. W. Müller, "Receuil des Conférences du 17$^e$ Colloque de Pharmacie Industrielle", Geneva 1978, pp. 34–36. In addition, the claimed oil components, such as hexyl laurate, isopropyl myristate and laurate are known as penetrants from ointment and macroemulsion technology.

With the exception of the unnecessary homogenization, the processes for the preparation of the microgels given in DE-OS No. 3,212,053 do not differ from the preparation of macroemulsion systems with coemulsifiers. The mixtures referred to in the examples give transparent, semisolid gel systems, which are erroneously called microemulsions.

It is also known that the use of saturated alcohols with a chain length of more than 10 carbon atoms as the cosurfactant does not at room temperature permit the formation of microemulsions with a sufficiently broad concentration range, due to the low diffusion rate of said alcohols into the interface, cf K. S. Birdi, Colloid & Polymer Sci., 260, 629, 1982; S. Candau and R. Zana, Colloid Sci., 84, 206, 1981. If this were not the case, then all the problems would have been solved through the use as the cosurfactant of lauryl alcohol, the first non-toxic alcohol in the series. However, the formation of a microemulsion at room temperature is only possible with dodecanol.

The problem of the present invention is to provide pharmaceutical multicomponent systems, which are stable and physiologically unobjectionable at room temperature and which improve the biological availability of the active agents contained therein compared with known systems.

This problem is solved by the liquid, transparent multicomponent systems according to claim 1.

It has been found that the penetration of a pharmaceutical active agent through the skin is sped up, if it is applied in dissolved form. The depot character of the corneal layer is retained and the passage into and through the membrane is aided, so that it is also possible to absorb molecules with low diffusion coefficients. If the systems according to the invention are administered perorally or parenterally, there is a supersaturation of the solution with active agent on diluting with the aqueous phase, namely gastric juice or serum, so that in this way a good availability of the drug can be obtained.

Compared with the gel system described in DE-OS No. 3,212,053, the invention has led to a surprising increase in the biological availability both from the anhydrous, oil-rich systems and from the water-rich, highly liquid systems (cf comparison example 1 and FIG. 1). This is probably firstly brought about by the low viscosity and the surface-active characteristics of the system leading to a rapid penetration through the cornea and secondly by the fact that an increased thermodynamic activity of the active agent occurs through the saturation concentration of said agent in the system being exceeded through modifying the water concentration.

Anhydrous solutions containing lipophilic active agents in dissolved form are preferably applied to the skin under occlusive conditions, e.g. by means of an impermeable plaster. The water penetrating from the skin into the system reduces the solubility of the active agent and consequently leads to a supersaturated solution. However, on dissolving water-soluble active agents in an aqueous system and applying same to the skin, active agent supersaturation is also obtained by the evaporation of part of the water.

The special properties of the systems according to the invention are based on the use of certain surfactant-/cosurfactant combinations. According to the invention, the surfactant is constituted by a polyoxyethylated glycerol ester and/or ether with aliphatic ($C_6$–$C_{22}$) carboxylic acids or alcohols and more than 7 to max 40 ethylene oxide units. All nonionic surfactants with a HLB value of above 8, particularly PEG glycerol esters, PEG fatty acid esters, PEG fatty alcohol ethers, ethoxylated cholesterols, sugar esters and ethylene oxide-propylene oxide block polymers are fundamentally suitable as the surfactant component. Amphoteric compounds, such as fatty acid-amidoalkyl-betaines with $C_2$–$C_{22}$ fatty acids or lecithin derivatives are also suitable as surfactants.

However, the formation of the systems according to the invention is only possible in combination with certain cosurfactants, namely partial esters or ethers of polyhydric alcohols with fatty acids or fatty alcohols with 4 to 22 carbon atoms, particularly 8 to 10 carbon atoms, as well as mixtures thereof. It is only possible not to use the cosurfactants, if oleyl alcohol and/or polar esters of monohydric alcohols with 2 to 4 C-atoms with fatty acids with 8 to 18 C-atoms are present as the oil component and low molecular weight polyoxyethylene/polyoxypropylene copolymers are present as the surfactant component.

Examples of preferred multicomponent systems according to the invention are given hereinafter:

1. Formulations of PEG (20 EO)-oleic acid glycerol partial esters, caprylic-capric acid partial esters or medium-chain triglycerides, isopropyl palmitate and water.
2. Formulations of PEG (250)-soysterol, caprylic-capric acid partial esters, isopropyl myristate and water.
3. Formulations of PEG (20 EO)-lauric acid glycerol partial esters, caprylic-capric acid glycerol partial esters, isopropyl palmitate and water.
4. Formulations of polyoxyethylene/polyoxypropylene copolymers with a molecular weight of the polyoxypropylene fraction of 1200 and a polyoxyethylene fraction of 20 to 40% by weight, based on the total weight of the copolymer, oleyl alcohol and water. The oleyl alcohol forms both the oil component and the cosurfactant in this system.

According to the invention, the term "oil component" means lipophilic, water-immiscible liquids and the term "aqueous component" covers hydrophilic, polar liquids.

Suitable oil components are higher viscous and less viscous aliphatic hydrocarbons, synthetic and natural oils, such as olive oil, peanut oil, rape oil, etc as well as in particular oleyl oleates, isooctyl stearate, hexyl laurate, di-n-butyl adipate, isopropyl myristate, palmitate and stearate, triglyceride mixtures of saturated and unsaturated fatty acids with 4 to 22 carbon atoms, oleyl alcohol, ethereal oils, isopropyl caprylate, isopropyl caprinate, isopropyl laurate and others.

Single-phase ranges with different water concentrations can be obtained as a function of the mixing ratio used and the nature of the surfactant components used.

FIG. 2 shows a three-component diagram for the water/isopropyl stearate system with a 3:7 mixture of PEG (20 EO)-glycerol monooleate and capric-caprylic acid glycerol ester with a 40% monoglyceride proportion. In this diagram the coloured areas represent the single-phase areas at ambient temperature (28° C.).

The nature and concentration of the coemulsifiers of the surfactant and cosurfactant determine both the scope of the thermodynamic, stable, single-phase range and also the viscosity of the system and the temperature range in which there is thermodynamic stability. A system with the lowest surfactant concentration in a temperature range up to at least 40° C. is the most suitable for pharmaceutical use. On heating a single-phase system, without modifying the concentration of the components, as a function of the composition it changes over to a multiphase system at a given temperature, the individual phases separating in different ways. On cooling, the original, single-phase system is formed again. The systems behave in the same way towards the lower temperature range. Here also, the original transparent system is formed again after redissolving the crystallized surfactants.

The liquid, transparent multicomponent systems according to the invention can be prepared in that initially the surfactant, cosurfactant and oil phase are mixed together and then the active agent or agents are dissolved in this mixture. Slight heating can be useful for dissolving the solid surfactants, as well as the pharmaceutical active agent or agents. If present, the aqueous phase is incorporated at the end at room temperature. When preparing the systems according to the invention, it is advantageous compared with known gels and macroemulsions, that the preparation takes place without significant energy expenditure and homogenization is unnecessary. Through the choice and concentration of the components used, it is possible to control the viscosity and temperature range at which the formulation is stable.

As the dissolved active agent acts as an additional component in the system according to the invention, as a function of the character of the substance, the concentration range of the single-phase area is displaced. As yet, no conformities with a particular law have been found, so that the optimum concentration of the components water, oil and coemulsifier must be determined afresh for each active agent. For this purpose, a mixture of 30 to 50% by weight of oil is brought together with the surfactant and cosurfactant at a ratio of approximately 2:3. The particular active agent is then dissolved in this system up to saturation. This is followed by the addition of approximately 50% by weight water and observation takes place as to whether there is a water separation or an oil separation. In the first case, further cosurfactant is added and in the second further surfactant until a single-phase system forms. It is easily possible in this way to determine the optimum composition for each system.

Generally, systems according to the invention contain up to 70% by weight of an oil component, up to 85% by weight of an aqueous component, 5 to 60% by weight of a coemulsifier of a surfactant with a HLB value >8 (5 to 95% weight, based on the coemulsifier) and a cosurfactant with a HLB value <8 (5 to 95% by weight, based on the coemulsifier).

The particular active agent concentration is a function of the therapeutical requirements, as well as the saturation solubility of the active agent in the system. It is already known of ionic coemulsifier systems, which have undergone detailed colloid-chemical investigation, that the oil component in the boundary layer can participate in the cosurfactant function, cf S. Levine and K. Robinson, J. Phys. Chem. 76,877, 1972; J. R. Hansen, J. Phys. Chem. 73, 256, 1974. The described oil component acts in a similar way in the system according to the invention, so that as a function of the oil phase composition, the single-phase range is displaced and in certain circumstances, the cosurfactant proportion or oil proportion can be reduced and it is even possible to eliminate the latter.

Physiologically acceptable, lipophilic compounds, which are liquid at room temperature are suitable as oil components and in particular
  (a) natural oils, such as peanut, olive, castor, sesame, rape, ethereal and similar oils;
  (b) semisynthetic and synthetic mono, di and triglycerides of saturated and unsaturated ($C_6$–$C_{22}$) fatty acids, as well as their ethoxylated derivatives;
  (c) liquid waxes, such as isopropyl myristate, caprinate, caprylate, laurate, palmitate and stearate; oleates, e.g. oleyl oleate, ethyl oleate, etc;
  (d) monohydric and polyhydric aliphatic alcohols, such as hexadecyl alcohol, 2-octyldodecanol, oleyl alcohol, etc, as well as their ethoxylated derivatives;
  (e) aliphatic ($C_4$–$C_{10}$) carboxylic acids, as well as their ethoxylated derivatives.

The systems according to the invention can also contain stabilizers. Apart from antioxidants and preservatives, these can also be buffer substances and isotonic agents. Furthermore, for the chemical stabilization of the active agent or active agent mixture, it is possible to incorporate special stabilizers, such as e.g. tartaric acid, in conjunction with ergotamine tartrate or sodium polyphosphate, in conjunction with phenyl butazone.

All suitable active agents for local and systemic action can be incorporated into the systems according to the invention. Cutaneous, peroral, parenteral, vaginal or rectal administration are possible. In the case of cutaneous application, the action control takes place both locally and systemically via the concentration of the aqueous phase, the nature of the oil component and the composition of the coemulsifier. In a formulation of the system according to the invention, for transdermal use of hydrophilic active agents or for the cutaneous, local use of lipophilic active agents, the components are present with the following concentrations:
  0.01 to 15% by weight of solid active agent or up to 65% by weight of liquid active agent,
  2.5 to 40% by weight of surfactant,
  0 to 45% by weight of cosurfactant,
  0 to 35% by weight of oil components,
  40 to 80% by weight of water,
  the sum of the cosurfactant and oil components representing at least 2.5% by weight.

In place of water, it is also possible to use aliphatic, monohydric or polyhydric $C_2$–$C_4$-alcohols or urea alone, in combination or in combination with water.

In the case of lipophilic active agents which are not to act automatically, the aim is the formulation of a system, which rapidly penetrates the stratum corneum and leads to an active agent supersaturation. Examples for active agents usable in this way are cortisones, antipsoriatics, antimycotics, salicylates, cytostatics, antibiotics, virustatics, antihistamines, UV-absorbers, chemotherapeutics, antiseptics, estrogens, antihydrotics, ethereal oils and scar treatment agents.

In systems according to the invention for transdermal (systemic) use of lipophilic active agents, the components can be present up to the saturation of active agent in the following concentrations:
  0.1 to 15% by weight of solid active agent or up to 65% by weight of liquid active agent,
  1 to 50% by weight of surfactant,
  0 to 80% by weight of cosurfactant,
  0 to 85% by weight of oil components,
  the sum of the cosurfactant and oil components being at least 2.5% by weight.

Examples for active agents systemically usable according to the invention are antirheumatics, antiphlogistics, $\beta$-blockers, antiemetics, antiarrythmics, anthelmintics, cardiants, spasmolytics, thrombocyte aggregation inhibitors, ethereal oils and all substances with a high first pass effect.

The application of the systems according to the invention to the skin can e.g. take place with dosing aerosols or sprays, as well as in plaster form. In the latter case, the liquid formulation is absorbed by the pores of a foam-like carrier fleece in the reservoir of a plaster formulation.

Following the removal of the protective film, this carrier is applied directly to the skin, without any control membrane. The colloidal solution migrates, as a function of its composition, at a given speed into the stratum corneum and the latter ensures a constant active agent transport. The stratum corneum virtually assumes the function of a control membrane, but control is based on the composition of the formulation. The inventive systems for oral and parenteral administration differ little with regard to the concentration of the components from the aforementioned systems. In this case, the aim is formulation of systems which, when diluted with gastric juice or serum, form very finely disperse O/W macroemulsions, which up to the saturation solubility enclose the active agent and release it in a delayed manner. As a result of their interfacial behaviour, such highly disperse systems can be called self-emulsifying and they form finely disperse emulsions with an approximately constant particle size distribution of the inner phase.

An organoleptic selection of the surfactant and cosurfactants is necessary for peroral administration, e.g. as drops or in gelatin capsules. In the case of parenteral administration, it must be ensured that the surfactants do not lead to any significant hemolytic activity.

According to a further embodiment of the invention, it is also possible to use those systems no longer having an oil phase and in which only the cosurfactant component is of a lipophilic nature. These are particularly suitable for oral, parenteral percutaneous and particularly rectal administration.

In such systems, the concentration range limits for the components are much narrower:
1 to 5% by weight active agent,
3 to 30% by weight surfactant,
10 to 45% by weight cosurfactant,
50 to 70% by weight water.

The formulations can either be administered as an enema or in the case of formulations with a low water percentage as a rectal capsule.

The invention is further illustrated by means of the following examples.

EXAMPLE 1

Various multicomponent systems according to the invention were prepared in which, unless otherwise stated, initially a mixture of surfactant, cosurfactant, oil component and optionally active agent is prepared at room temperature and then the water is optionally added. The following formulations were prepared:

| Formulation I | |
|---|---|
| PEG(20 EO)-oleic acid glycerol partial esters | 40% by weight |
| Caprylic-capric acid glycerol partial esters (42% monoglyceride content) | 24% by weight |
| Medium-chain triglyceride | 16% by weight |
| Water | 20% by weight |
| Formulation II | |
| PEG(20 EO)-oleic acid glycerol partial esters | 25% by weight |
| Caprylic-capric acid glycerol partial esters (42% monoglyceride content) | 15% by weight |
| Medium-chain triglyceride | 10% by weight |
| Water | 50% by weight |
| Formulation III | |
| Isosorbide dinitrate | 3.5% by weight |
| PEG(20 EO)-oleic acid glycerol partial esters | 23.2% by weight |
| Caprylic-capric acid glycerol partial esters (42% monoglyceride content) | 34.8% by weight |
| Isopropylpalmitate | 38.5% by weight |
| The isosorbide dinitrate was dissolved, accompanied by heating, in the surfactant, cosurfactant and oil component mixture. | |
| Formulation IV | |
| PEG(20 EO)-oleic acid glycerol partial esters | 24% by weight |
| Caprylic-capric acid glycerol partial esters (40% monoglyceride content) | 16% by weight |
| 1,2-propylene glycol | 60% by weight |
| Water | Random |
| Formulation V | |
| Indomethacin | 2.5% by weight |
| PEG(20 EO)-oleic acid glycerol partial esters | 24% by weight |
| Caprylic-capric acid glycerol partial esters (40% monoglyceride content) | 15% by weight |
| Medium-chain triglycerides | 10% by weight |
| Water | 48.5% by weight |
| Formulation VI | |
| Indomethacin | 4.0% by weight |
| Polyoxyethylene/polyoxypropylene copolymer (30% by weight · mol. wt. 1200) | 48.0% by weight |
| Oleyl alcohol | 48.0% by weight |
| Formulation VII | |
| PEG(20 EO)-oleic acid glycerol partial esters | 12.5% by weight |
| Caprylic-capric acid glycerol partial esters (42% monoglyceride content) | 23.5% by weight |
| Isopropyl myristate (oil component) | 10.0% by weight |
| Eucalyptus oil (oil component) | 10.0% by weight |
| Pine-needle oil (oil component) | 10.0% by weight |
| Camphor | 3.0% by weight |
| Menthol | 3.0% by weight |
| Water | 28.0% by weight |

Menthol and camphor were dissolved at room temperature into the mixture of ethereal oil, surfactant and cosurfactant and the water was added at the end.

This formulation can be used as a balneotherapeutic or as an inhaling agent. In a commercial inhaler mixed with hot water, the delivery of the ethereal oil in the vapour phase is extended up to 5 times by the miscellar inclusion when forming the macroemulsion, compared with the use of an identical ethereal oil composition in an ointment base.

| Formulation VIII | |
|---|---|
| Polypeptide hirudin (10,000 ATE = 0.7 g) | 0.073% by weight |
| PEG(25 EO)-soysterol | 26.0% by weight |
| Caprylic-capric acid glycerol partial esters (40% monoglyceride content) | 30.8% by weight |
| Isopropylpalmitate | 30.9% by weight |
| Water | 12.227% by weight |
| Formulation IX | |
| PEG(20 EO)-oleic acid glycerol partial esters | 11.0% by weight |
| Caprylic acid monoglyceride (90% monoglyceride content) | 16.0% by weight |
| Isopropyl stearate | 18.0% by weight |
| Water | 55.0% by weight |
| Formulation X | |
| Isopropanol | 20% by weight |
| Lecithin | 10% by weight |
| Isopropylpalmitate | 40% by weight |
| Water | 30% by weight |
| Formulation XI | |
| Soyphosphatides (70 to 75% phosphatidyl choline) | 6.9% by weight |
| Isopropylpalmitate | 24.9% by weight |
| Isopropanol | 28.0% by weight |
| Water | 42.0% by weight |

EXAMPLE 2

In vitro proof of the absorption of a macromolecule by active transport from the highly disperse multicomponent system according to the invention.

5 ml of formulation VIII according to example 1 were compared in a sartorious sedimentation balance with a surface of 87.5 cm$^2$ with 10 ml of a phosphate buffer with a pH-value of 7.6 as an artificial blood phase. Fresh, non-scalded pig skin taken approximately 1 hour after the death of the animal was used as the membrane. The test was carried out at 32° C. and the hirudin concentration in the phosphate buffer was measured over a period of 48 hours. The results are given in table 1.

TABLE 1

| Time (h) | Concentration (ATE/ml) |
|---|---|
| 2 | 3–4 |
| 6 | 12 |

TABLE 1-continued

| Time (h) | Concentration (ATE/ml) |
|---|---|
| 12 | 19 |
| 24 | 24 |

It was established that the hirudin passage was largely independent of the thickness of the pigskin used. No macromolecule transport could be observed 48 hours after the death of the animal. On the basis of the results, it was concluded that there is an active or carrier-imparted transport of the polypeptide molecule through the still living pigskin.

EXAMPLE 3

Indomethacin absorption after oral administration of the active agent in the highly disperse multicomponent system according to the invention in humans.

1 g of formulation V according to example 1 in a hard gelatin capsule was orally administered to male test subjects. The indomethacin level in the serum was then determined by means of high pressure liquid chromatography. The results are given in table 2.

TABLE 2

| Time after administration | Plasma concentration ($\mu g\ ml^{-1}$) |
|---|---|
| 30 min | 0.6 ± 0.3 |
| 60 min | 1.0 ± 0.4 |
| 120 min | 1.7 ± 0.6 |
| 180 min | 2.5 ± 0.6 |
| 4 h | 2.2 ± 0.7 |
| 6 h | 1.8 ± 0.5 |
| 8 h | 1.5 ± 0.4 |
| 12 h | 0.7 ± 0.2 |

The results show a clear delayed action.

COMPARISON EXAMPLE 1

The absorption of tritium-labelled arecaidine n-propylester-HCl from the following systems was investigated:
A Formulation I of example 1 (oil-rich)
B Formulation II of example 1 (water-rich)
C "Microgel" according to DE-OS No. 3,212,053 with the following composition:
PEG-oleyl ether (Brij 97): 23.2% by weight
Isopropyl laurate: 23.2% by weight
Dodecanol: 7.3% by weight
Water: 46.3% by weight
D Macroemulsion using the same components as in formulations I and II of example 1:
PEG (20 EO)-oleic acid glycerol partial esters: 25% by weight
Caprylic-capric acid glycerol partial esters: 15% by weight
Medium-chain triglycerides: 15% by weight
Water: 45% by weight
E Aqueous wool wax alcohol ointment according to DAB 8.

Tritium-labelled arecaidine-n-propylester-HCl was incorporated in such a quantity into each of the formulations that a radio-activity of 1 $\mu$Ci/4 g of formulation was obtained. In each case, 3.5 g of each formulation was applied to 100 cm$^2$ of shaved skin of 3 rabbits (weight 3.5 kg). The tritium activity in the serum of the treated animals was then measured on in each case 0.2 ml of serum for a total of 7 hours at 1 hour intervals. The mean value of the results obtained on 3 animals were determined in counts/min for each formulation. The results are shown graphically in FIG. 1.

It is revealed that the biological activity of the applied active agent of the system according to the invention is significantly higher than that from the known systems. This applies both to the oil-rich formulation (A) and the water-rich formulation (B) according to the invention.

The configuration of the serum level concentrations indicates a steady state and therefore a delayed release at an increased level.

COMPARISON EXAMPLE 2

Absorption of isosorbide dinitrate in the case of cutaneous application to humans.

Use was made of the isosorbide dinitrate-containing formulation III of example 1 according to the invention, as well as a commercial ointment formulation (ISO-KET®-ointment) containing the active agent in the same quantity. The formulations were in each case cutaneously applied to three test subjects. The highly disperse system according to the invention was applied to 150 cm$^2$ skin surface in a quantity containing 100 mg of active agent, whilst the same active agent quantity in the commercial ointment formulation was applied to 400 cm$^2$.

The 5-isosorbide-mononitrate concentration in the serum of the test subjects was then gas chromatographically determined for in each case 24 hours and the mean values were calculated for each of the formulations. The results are graphically given in FIG. 3.

It was found that the active agent concentration in the blood plasma of the test subjects was much higher following the application of the formulation according to the invention than following the application of the commercial ointment. although the available absorption surface was smaller by a factor of 2.6 in the first case.

We claim:
1. A multicomponent system for pharmaceutical use comprising:
at least one pharmaceutically active agent,
0 to 70% by weight of at least one oil component,
2 to 60% by weight of at least one physiologically acceptable surfactant selected from the group consisting of nonionic surfactants with an HLB value higher than 8 and amphoteric surfactants, and
0 to 78% by weight of at least one cosurfactant selected from the group consisting of partial esters and ethers of polyhydric alcohols with saturated or unsaturated fatty acids and fatty alcohols with 6 to 22 C-atoms said at least one cosurfactant being liquid below 40° C.,
wherein the individual components are present in such quantities in said system that at room temperature stable, liquid, single-phase systems are formed, which contain said at least one pharmaceutically active agent in dissolved form,
and wherein the sum of said at least one oil component and said at least one cosurfactant is at least 10% by weight.

2. A multicomponent system according to claim 1, wherein said at least one surfactant is selected from the group consisting of ethoxylated glycerol partial esters and ethers with aliphatic carboxylic acids and alcohols with 2 to 22 C-atoms and with more than 7 and up to 40 ethylene oxide units.

3. A multicomponent system according to claim 1, wherein said at least one surfactant is selected from the group consisting of polyethylene glycol esters and ethers with aliphatic carboxylic acids with 6 to 22 C-atoms and with aliphatic alcohols with 6 to 22 C-atoms.

4. A multicomponent system according to claim 1, wherein said at least one surfactant is selected from the group consisting of ethoxylated cyclopentano-perhydrophenanthrene derivatives with 5 to 50 ethylene oxide units.

5. A multicomponent system according to claim 1, wherein said at least one surfactant is selected from the group consisting of polyoxyethylene/polyoxypropylene copolymers.

6. A multicomponent system according to claim 1, wherein said at least one surfactant is selected from the group consisting of acid-amidoalkyl-betaines with ($C_2$-$C_{22}$) fatty acids.

7. A multicomponent system according to claim 1, wherein said at least one cosurfactant is selected from the group consisting of partial esters and ethers of polyhydric alcohols with saturated fatty acids and alcohols with 8 to 10 C-atoms.

8. A multicomponent system according to claim 1, wherein said at least one cosurfactant is selected from the group consisting of glycerol partial esters and ethers with fatty acids and fatty alcohols with 8 to 10 C-atoms.

9. A multicomponent system according to claim 1, wherein said at least one cosurfactant is selected from the group consisting of caprylic and capric acid glycerol esters, and mixed capric-caprylic acid glycerol partial esters.

10. A multicomponent system according to claim 1, wherein said at least one surfactant is selected from the group consisting of PEG (20 EO)-oleic acid glycerol partial esters, and said at least one cosurfactant is selected from the group consisting of capric-caprylic acid glycerol partial esters.

11. A multicomponent system according to claim 1, wherein said at least one oil component is selected from the group consisting of oleyl alcohol and polar esters of monohydric alcohols with 2 to 4 C-atoms with fatty acids having 8 to 12 C-atoms and, said at least one surfactant is selected from the group consisting of low molecular weight polyoxyethylene/polyoxy propylene copolymers with a PEG proportion of 20 to 50% by weight, based on the copolymer, and a propylene fraction molecular weight of 600 to 1400.

12. A multicomponent system as in claim 11 wherein said at least one oil component serves as said at least one cosurfactant in said system.

13. A multicomponent system according to claim 1, further comprising at least one member from the group consisting of water and at least one hydrophilic component.

14. A multicomponent system according to claim 13, wherein said at least one hydrophilic component is selected from the group consisting of an aliphatic monohydric or polyhydric $C_2$-$C_4$-alcohol, urea and water.

15. A multicomponent system according to claim 1, further comprising from 1 to 85% by weight of water.

16. A multicomponent system according to claim 1, further comprising 35 to 95% by weight of water.

17. A multicomponent system according to claim 1 for use in preparations of pharmaceutical formulations for cutaneous, peroral, parenteral, vaginal or rectal administration, as well as inhalations, balneotherapeutics and cosmetic products.

18. A multicomponent system according to claim 17, wherein said system is an anhydrous system for use under occlusive conditions for the transdermal application of lipophilic active agents.

19. A multicomponent system according to claim 17, wherein said system is an aqueous system for application in open form for the transdermal application of hydrophilic active agents.

20. A multicomponent system according to claim 17, wherein said system is an aqueous system used for local cutaneous application.

21. A multicomponent system according to claim 1 wherein said at least one surfactant is physiologically acceptable, and is selected from the group consisting of nonionic surfactants with an HLB value higher than 8, and amphoteric surfactants, and wherein at least one compound selected from the group consisting of oleyl alcohol and polar esters of monohydric alcohols with 2 to 4 C-atoms with 8 to 18 C-atoms, function(s) as both said at least one oil component and said at least one cosurfactant.

22. A multicomponent system according to claim 21 wherein said at least one surfactant is selected from the group consisting of low molecular weight polyoxyethylene/polyoxypropylene copolymers.

23. A multicomponent system for pharmaceutical use comprising
  0.1-15% by weight solid or up to 65% by weight liquid of at least one pharmaceutically active agent,
  up to 85% weight of at least one oil component,
  0-50% by weight of at least one physiologically acceptable surfactant selected from the group consisting of nonionic surfactants with an HLB value higher than 8 and amphoteric surfactants, and
  up to 80% by weight of at least one cosurfactant selected from the group consisting of partial esters and ethers of polyhydric alcohols with saturated or unsaturated fatty acids and fatty alcohols with 6 to 22 C-atoms said at least one cosurfactant being liquid below 40° C., and
  wherein the sum of said at least one cosurfactant and said at least one oil component is at least 2.5% by weight, and the individual components are present in such quantities in said system that at room temperature stable, liquid, single-phase systems are formed, which contain said at least one pharmaceutically active agent in dissolved form.

24. Process for the preparation of a multicomponent system for pharmaceutical use comprising: at least one pharmaceutically active agent, 0 to 70% by weight of at least one oil component, 2 to 60% by weight of at least one physiologically acceptable surfactant selected from the group consisting of nonionic surfactants with an HLB value higher than 8 and amphoteric surfactants, and 0 to 78% by weight of at least one cosurfactant selected from the group consisting of partial esters and ethers of polyhydric alcohols with saturated or unsaturated fatty acids and fatty alcohols with 6 to 22 C-atoms, said at least one cosurfactant being liquid below 40° C., wherein the individual components are present in such quantities in said system that at room temperature stable, liquid, single-phase systems are formed, which contain said at least one pharmaceutically active agent in dissolved form, said process comprising the steps of:
  intermixing said at least one surfactant, said at least one cosurfactant, and said at least one oil component, and subsequently,
  dissolving said at least one pharmaceutically active agent in the mixture, and then
  adding water.

25. A process as in claim 24 wherein said dissolving step comprises the step of dissolving said at least one pharmaceutically active agent, accompanied by heating, in the mixture.

* * * * *

UNITED STATES PATENT AND TRADEMARK OFFICE
CERTIFICATE OF CORRECTION

PATENT : 4,719,239
DATED : January 12, 1988
INVENTOR(S) : Bernd W. W. Muller et al.

It is certified that error appears in the above-identified patent and that said Letters Patent is hereby corrected as shown below:

Column 12, line 14 (Claim 21, line 8), after "to 4 C-atoms with" insert --fatty acids having--.

Column 12, line 25 (Claim 23, line 6), "0-50%" should read --1-50%--.

Signed and Sealed this

Seventh Day of November, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 4,719,239
DATED : January 12, 1988
INVENTOR(S) : Bernd W.W. Muller et al.

It is certified that error appears in the above-identified patent and that said Letters Patent is hereby corrected as shown below:

Column 11, line 61, (Claim 16, line 2), change "35 to 95%" to --35 to 85%--.

Signed and Sealed this

Sixteenth Day of January, 2001

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO.    : 4,719,239
DATED         : January 12, 1998
INVENTOR(S)   : Bernd W. W. Muller et al.

It is certified that error appears in the above-identified patent and that said Letters Patent is hereby corrected as shown below:

Claim 21, column 12,
Line 14, (claim 21, line 8), after "with" insert -- fatty acids having --.

Claim 23, column 12,
Line 25, (claim 23, line 6) "0-50%" should read --1-50% --.

Column 11,
Line 61, (claim 16, line 2), change "35 to 95%" to -- 35 to 85% --.

Signed and Sealed this

Second Day of October, 2001

Attest:

NICHOLAS P. GODICI
*Attesting Officer*  *Acting Director of the United States Patent and Trademark Office*